US00PP33703P2

(12) United States Plant Patent
Dirr et al.

(10) Patent No.: US PP33,703 P2
(45) Date of Patent: Nov. 30, 2021

(54) ***HYDRANGEA* PLANT NAMED 'BAILMACSIX'**

(50) Latin Name: *Hydrangea macrophylla*
Varietal Denomination: Bailmacsix

(71) Applicant: Bailey Nurseries Inc., Newport, MN (US)

(72) Inventors: Michael A. Dirr, Bogart, GA (US); Jeff Beasley, Lavonia, GA (US); Mark Griffith, Watkinsville, GA (US); Rhonda Helvick, Madison, GA (US); Oren McBee, Bishop, GA (US); David Jonathan Roberts, Athens, GA (US); Justin Schulze, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 17/236,045

(22) Filed: Apr. 21, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Bailmacsix' that is characterized by its compact plant habit; reaching 40 cm to 92 cm in height and width, its cold hardiness in U.S.D.A. Zone 4, its blooming on both old and new wood, and its inflorescences that are deep pink or deep blue/purple depending on growing conditions.

2 Drawing Sheets

Botanical classification: *Hydrangea macrophylla.*
Varietal denomination: 'Bailmacsix'.

BACKGROUND OF THE INVENTION

The present invention relates to a new and distinct cultivar of *Hydrangea macrophylla* and will be referred to hereafter by its cultivar name, 'Bailmacsix' . 'Bailmacsix' represents a new lacecap type *Hydrangea*, a deciduous shrub grown for use as a landscape plant.

'Bailmacsix' was derived from an ongoing breeding program conducted by the Inventors in Watkinsville, Ga. The objectives of the breeding program are to develop new cultivars of *Hydrangea macrophylla* with compact plant habits, re-blooming habits, and cold hardiness in U.S.D.A. Zone 4.

'Bailmacsix' originated as a seedling that arose from seed planted from open pollination of an unnamed and unpatented plant of *Hydrangea macrophylla* from the Inventors' breeding program; reference no. TNSXMP0309, in June of 2013. The male parent is therefore unknown. 'Bailmacsix' was selected as a single unique plant in September of 2014 from the resulting seedlings.

Asexual propagation of the new cultivar was first accomplished by softwood stem cuttings by one of the Inventors in Watkinsville, Ga. in summer of 2016. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailmacsix' as a unique cultivar of *Hydrangea.*

1. 'Bailmacsix' exhibits a compact plant habit; reaching 40 cm to 92 cm in height and width.
2. 'Bailmacsix' exhibits cold hardiness in U.S.D.A. Zone 4.
3. 'Bailmacsix' exhibits blooming on both old and new wood.
4. 'Bailmacsix' exhibits inflorescences that are deep pink or deep blue/purple depending on growing conditions.

The female parent of 'Bailmacsix' differs from 'Bailmacsix' in having leaves that are lighter green in color, flowers that are lighter pink or blue/purple in color, fewer sterile flowers, stems and leaves that are less stiff, and in taking a longer time to bloom on new growth. 'Bailmacsix' can be most closely compared to the *Hydrangea macrophylla* cultivars 'PIIHM-I' (U.S. Plant Pat. No. 20,176) and 'Mini Penny' (U.S. Plant Pat. No. 15,744). 'PIIHM-I' is similar to 'Bailmacsix' in having lace-cap type flowers and blooms on new growth. 'PIIHM-I' differs from 'Bailmacsix' in having a larger plant size, longer internodes, and stems that are red in color and in being slower to bloom on new growth. 'Mini Penny' is similar to 'Bailmacsix' in having a compact habit and in being a remontant bloomer (new and old wood). 'Mini Penny' differs from 'Bailmacsix' in having mophead shaped inflorescences, cold hardiness only to U.S.D.A. Zone 5, and sterile flower sepals that are lighter pink and blue in color.

BRIEF DESCRIPTION OF THE DRAWINGS

The accompanying color photographs illustrate the overall appearance and distinct characteristics of the new *Hydrangea.*

The photograph in FIG. 1 was taken of a 4-year-old plant as grown outdoors in a trial bed in Cottage Grove, Minn. and provides a view of 'Bailmacsix' grown under non-blueing conditions.

Figure 1:
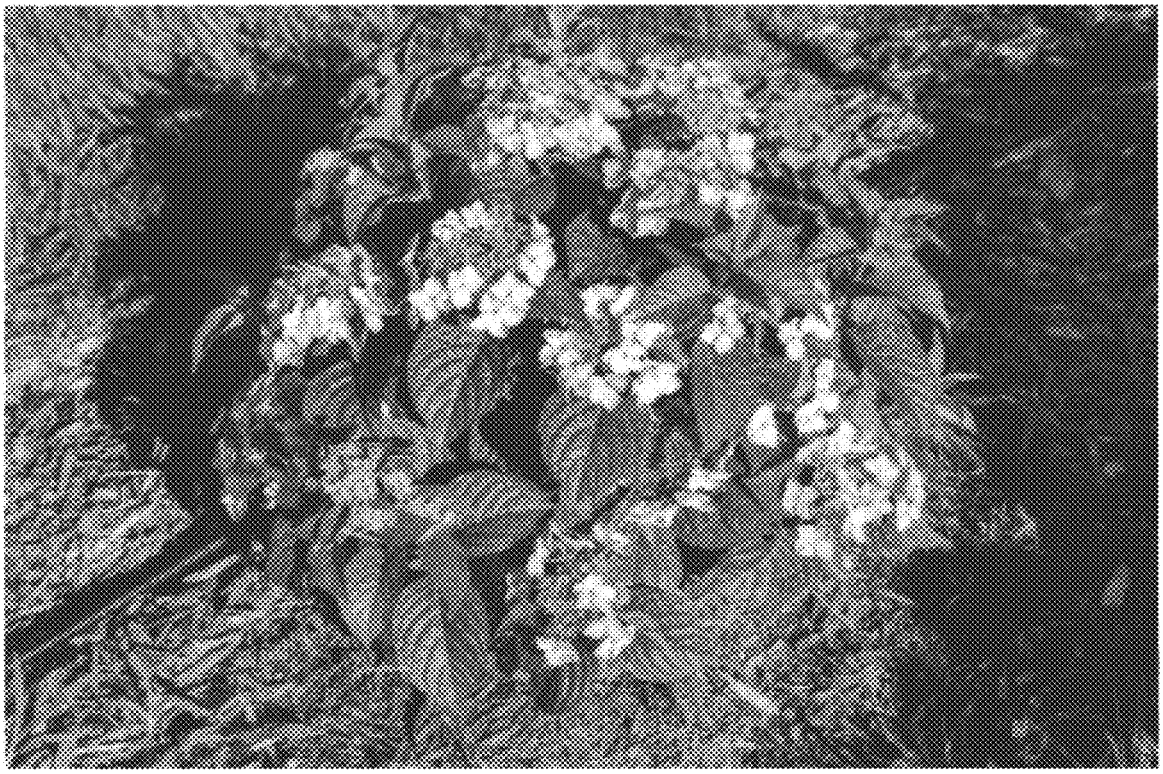
Figure 2:
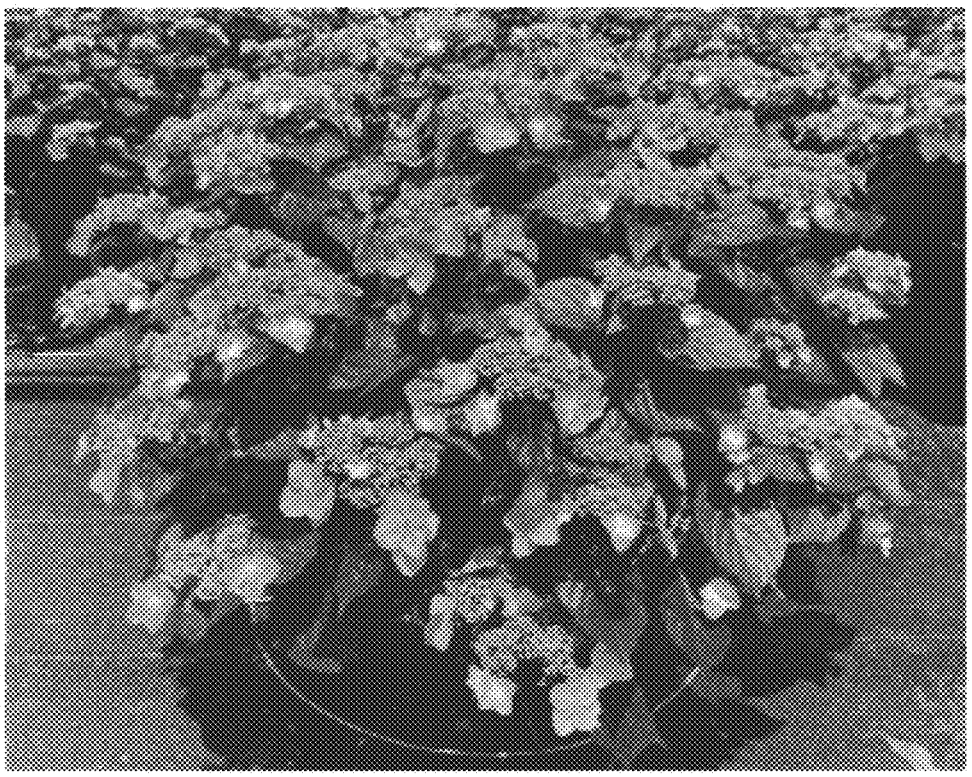

The photograph in FIG. 2 was taken of a 2-year-old plant as grown outdoors in a 3-gallon container in Winterville, Ga. and provides a view of 'Bailmacsix' in bloom grown under blueing conditions.

Figure 3:
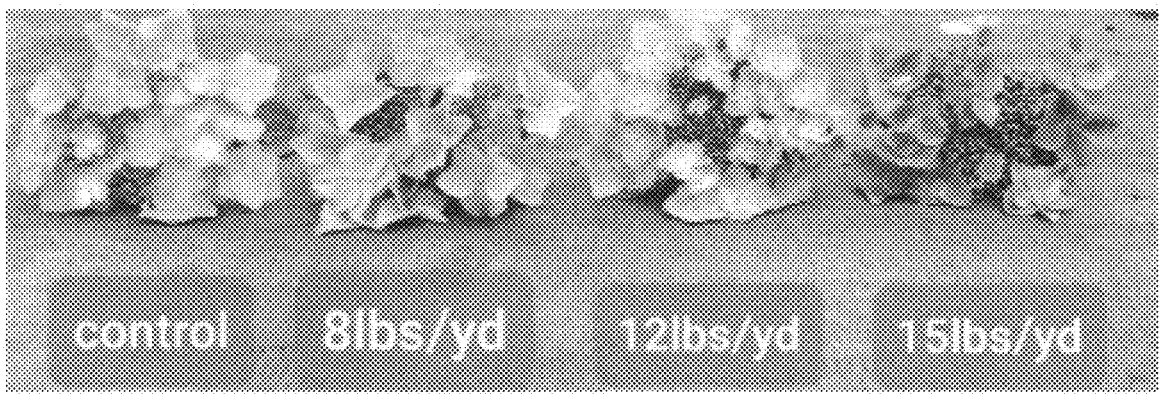

The photograph in FIG. 3 was taken of inflorescences from 2-year-old plants grown outdoors in 2-gallon containers in Yamhill, Oreg. with various levels of aluminum sulfate added to the soil and provides a view of the inflorescence color variations of 'Bailmacsix'.

The colors in the photographs may differ slightly from the color values cited in the detailed botanical description, which accurately describe the colors of the new *Hydrangea*.

BOTANICAL DESCRIPTION OF THE PLANT

The following is a detailed description of 2.5-year-old plants of 'Bailmacsix' as grown outdoors in 2-gallon containers in a greenhouse in Cottage Grove, Minn. The data was primarily taken on plants were grown in alkaline soils with some additional data provided when plants were grown in acidic soil with sufficient aluminum sulfate (blueing conditions). The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Early-summer on old wood and continues through fall on new wood; June to October in Georgia and July to September in Minnesota.

*Plant type.*—Deciduous shrub, mophead type *Hydrangea.*

*Plant habit.*—Compact.

*Height and spread.*—Reaches about 39 cm in height and 70 cm in spread as grown in a 2-gallon container, reaches reaching 40 cm to 92 cm in height and width as grown in the landscape in Georgia.

*Hardiness.*—At least to U.S.D.A. Zones 4 to 9.

*Diseases.*—No resistance or susceptibility to diseases has been observed.

*Root description.*—Fine and fibrous, 199B in color.

*Propagation.*—Softwood stem cuttings.

*Growth rate.*—Moderate.

*Root development.*—Softwood cuttings root readily in 6 weeks, rooted cuttings are overwintered and roots will fully develop in a one-quart container by mid-summer the following year.

Stem description:

*Stem shape.*—Rounded.

*Stem strength.*—Strong.

*Stem color.*—Young; 145A to 145B, mature; 144B, flushed with 183A, old growth at base; a blend of 199B and 200B.

*Stem size.*—Main branches; average of 12 cm in length, 1 cm in diameter, lateral branches; average of 13.5 cm in length, 4 mm in diameter.

*Stem surface.*—Younger and mature stems; glabrous, sparsely to moderately lenticellate, lenticles; 5 per $cm^2$, an average of 1.5 mm in length and 1 mm in width, 187A in color, old growth at base; bark-like, rugose, slightly peeling.

*Internode length.*—Average of 4.5 cm.

*Branching.*—Average of 5 main branches, average of 5 to 7 lateral branches per main branch.

*Stipules.*—Persistent, 2 opposite at base of petioles, stipule bud; is 5 mm in length, 1 mm in width, 183A in color, oblong in shape, acute apex, glossy and glabrous surface, stipule leaves; 1 cm in length, 4 mm in width, acute apex, serrate to entire margins, each leaf fused into base, opposite, both surfaces glossy, both surfaces 137A, base and veins 144B in color.

Foliage description:

*Leaf shape.*—Ovate.

*Leaf arrangement.*—Opposite.

*Leaf division.*—Simple.

*Leaf base.*—Attenuate.

*Leaf apex.*—Acute.

*Leaf margins.*—Serrate.

*Leaf venation.*—Pinnate, upper surface; 145B, lower surface; 145C in color, main vein flushed with 184A in color on both surfaces as it matures.

*Leaf size.*—Matures to an average of 10 cm in length and 5 cm in width.

*Leaf attachment.*—Petiolate.

*Leaf surface.*—Upper surface; glossy, lower surface; dull with a slight sheen.

*Leaf color.*—Young upper and lower surface; 144B, mature upper surface; center 144A, leaf color blends out towards the margins and tip darkening to 147A, mature lower surface; 147C to 147D.

*Petioles.*—An average of 1 cm in length and 3 mm in diameter, upper and lower surface color; young 145A, maturing to 185A in color, both surfaces glabrous and slightly shiny.

Inflorescence description:

*Inflorescence type.*—Terminal panicle, mophead in form, comprised of fertile flowers and single sterile flowers.

*Lastingness of inflorescence.*—Persistent for 3 months.

*Inflorescence number.*—One per lateral.

*Inflorescence size.*—Average of 8 cm in height, 14 cm in diameter.

*Flower number.*—Average of 50 sterile flowers and 150 fertile flowers per panicle.

*Flower fragrance.*—None.

*Flower aspect.*—Upright to outward.

*Flower size.*—Sterile flowers; an average of 4 cm in diameter and 5 mm in depth, fertile flowers; an average of 5 mm in diameter and 2 mm in depth.

*Flower type.*—Rotate.

*Flower buds.*—Sterile flowers; average of 3 mm in length and 4 mm in diameter, obovate in shape, color is 145B, fertile flowers; average of 3 mm in width and 2 mm in diameter, broad obovate in shape, a blend of 75A and 70A in color.

*Peduncles.*—Strong, average of 1 cm in length and 2 mm in width, color; 71A, surface is slightly shiny and moderately covered with very fine woolly hairs; 71A, or a blend of 71A and NN155A in color.

*Pedicels.*—Sterile flowers; strong, average of 2 cm in length and 1 mm in width, color; 68A, surface is slightly shiny and moderately covered with very fine woolly hairs that match surface color to NN155A in color, fertile flowers; strong, average of 3 mm in length and 1 mm in width, color; 68A, surface is slightly shiny and moderately covered with very fine woolly hairs that match surface color to NN155A in color.

*Petals.*—Sterile flowers; before opening; petal spot; 3 mm in diameter, round in shape, glabrous surface, young color is 145B, flushed with 63B at the top, mature color is a blend of 75A and 70A, when fully open; 3 mm in length, 2 mm in width, both surfaces are satiny and dull, acute apex, rotate arrangement, cuneate base, entire margins, ovate and concave in shape, inner and outer surface color a blend of 75A and 73B, fertile flowers; an average of 5, rotate arrangement, acute apex, cuneate base, entire margins, ovate and concave in shape, an average of 3 mm in length, 2 mm in width, upper and lower surface; glabrous, color; upper surface when opening upper and lower surface 73A to 73B, upper and lower surface when fully open N78C and 77D, for plants grown under blueing conditions; sterile petals 99A, fertile flowers 93B.

*Sepals.*—Sterile flowers; 4 to 5, broad rhomboidal in shape, moderately to strongly overlapping, rotate in arrangement, entire margin, apex is very slightly retuse to bluntly pointed, cuneate base, average of 2.3 cm in length and 2.5 cm in width, upper and lower surface glabrous and satiny, color: young upper and lower surface when opening and fully open; 145A and 145B, maturing upper surface fully open; base and mid-section NN155C with very light flushes of 10A, tips 68A, maturing lower surface fully open; base and mid-section NN155C with very light flushes of 10A, tips 68B, fully mature upper surface; 73A, veins 69B, fading to 69B, fully mature lower surface; a blend of 70C and 70D, veins N74A, fading to 69B, fertile flowers; 5, rotate in arrangement, ovate in shape, entire margin, acute apex, cuneate base, average of 0.5 mm in length and 1 mm in width, both surfaces are glabrous, color of upper and lower surface 11C, for plants grown under blueing conditions; sterile flowers upper surface outside edges 96A, centers 98A, base and veins 108D and NN155D, lower surface outside edges 92A, centers a blend of 101D and 108D, fertile flowers upper and lower surface 100A.

Reproductive Organs:

*Stamens.*—Sterile flowers; emerging from petal spot; 4 to 5, anther; broadly reniform in shape, 1 mm in length and width, N79A in color, filament; 4 mm in length, 0.5 mm in width and 84C and 64A in color, pollen is moderate in quantity and 155A in color, fertile flowers; average of 9, anther is broad reniform in shape, 0.6 mm in length and 79A in color with side stripes of N75A, filament is 4 mm in length and N74A and N75B in color, pollen is moderate in quantity and 155B in color.

*Pistils.*—Sterile flowers; emerging from petal spot; 3 to 4, average of 2 mm in length, 0.5 mm in width, stigma is round in shape and N74C in color, 0.5 mm in length and diameter, style is an average of 1.5 mm in length and N74A in color, ovary is 62B in color and inferior, fertile flowers; average of 4, an average of 2 mm in length, stigma is clavate in shape and 71A in color, style is 71A in color, ovary is 62C in color and inferior.

*Fruit and seed.*—Not observed.

It is claimed:

1. A new and distinct cultivar of *Hydrangea* plant named 'Bailmacsix' substantially as herein illustrated and described.

* * * * *